United States Patent [19]

Sprecker

[11] Patent Number: 4,735,932

[45] Date of Patent: Apr. 5, 1988

[54] ALLYL ESTER OF 2-CYCLOPENTYLOXYACETIC ACID COMPOSITIONS

[75] Inventor: Mark A. Sprecker, Sea Bright, N.J.

[73] Assignee: International Flavors & Fragrances Inc., New York, N.Y.

[21] Appl. No.: 52,987

[22] Filed: May 22, 1987

[51] Int. Cl.[4] .................................... A61K 7/46

[52] U.S. Cl. .................................... 512/26; 560/121; 562/503; 252/174.11; 523/102

[58] Field of Search .................... 252/522 R, 174.11; 560/121; 562/503; 512/26; 523/102

[56] References Cited

PUBLICATIONS

Luengo et al., Tet. Letters, vol. 25, pp. 4881–4884 (1984).

Khegman et al., J. Org. Chem., vol. 39, pp. 1772–1776 (1974).

*Primary Examiner*—James H. Reamer

*Attorney, Agent, or Firm*—Arthur L. Liberman

[57] ABSTRACT

Described are allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane, perfumery uses thereof and intermediates used in preparing said allyl ester, the allyl ester of 2-cyclopentyloxyacetic acid having the structure:

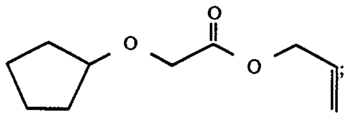

the 3,3-dimethyl-1-penten-4-oyl cyclohexane having the structure:

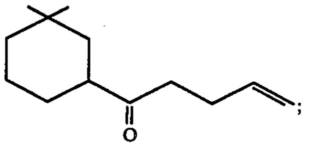

the methoxyisobutyl pyrazine having the structure:

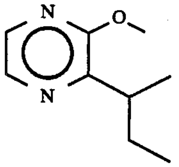

and the 3,3-dimethyl-1-(2-propenyl)-1-acetylcyclohexane having the structure:

5 Claims, 4 Drawing Sheets

GLC PROFILE FOR EXAMPLE I(A).
CRUDE

GLC PROFILE FOR EXAMPLE I (B).
CRUDE

NMR SPECTRUM FOR EXAMPLE I(B).

FIG. 4
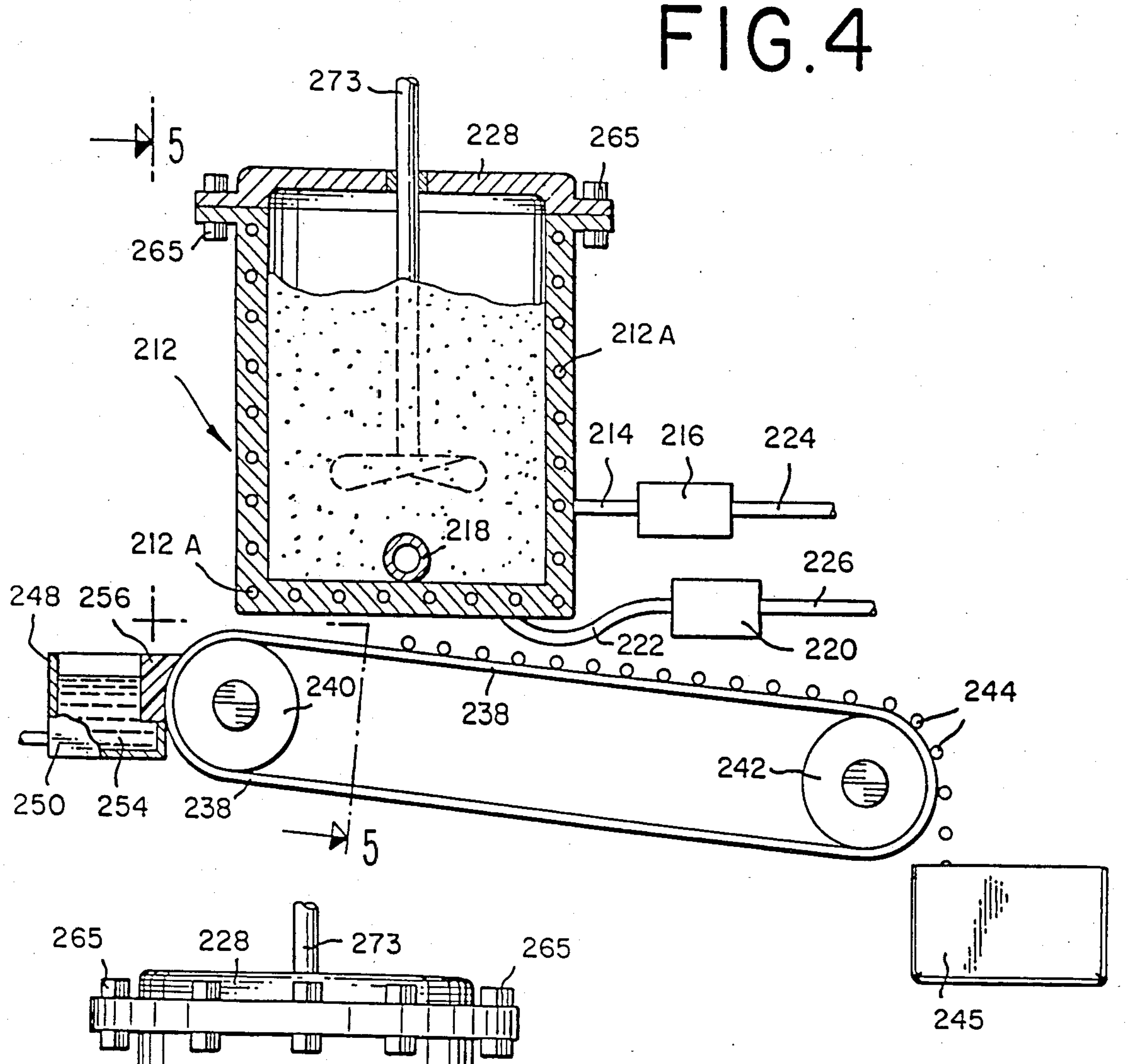
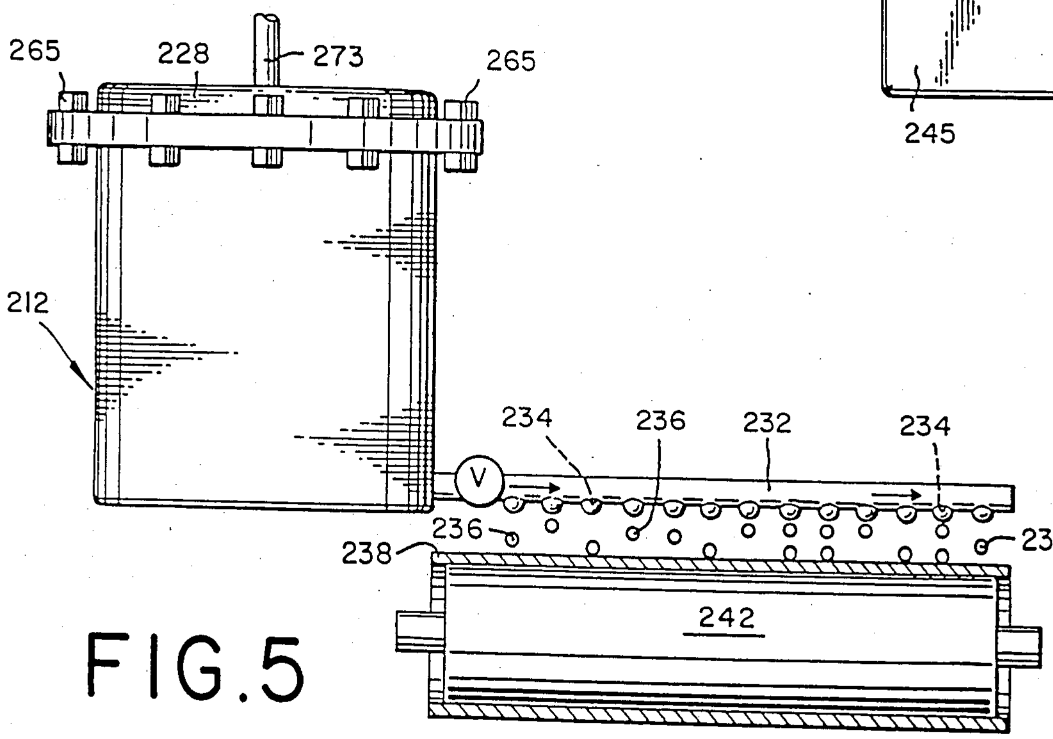
FIG. 5

ALLYL ESTER OF 2-CYCLOPENTYLOXYACETIC ACID COMPOSITIONS

BACKGROUND OF THE INVENTION

This invention relates to allyl ester of 2-cyclopentyloxyacetic acid, mixtures of same with 3,3-dimethyl-1-penten-4-oylcylohexane and/or methoxyisobutyl pyrazine and/or ob 3,3-dimethyl-1-(2-propenyl)-1-acetylcyclohexane and uses thereof in augmenting or enhancing the aroma of perfume compositions, perfumed articles and colognes.

Inexpensive rose, green apple and galbanum aromas with intense green, pineapple and galbanum undertones are highly desirable in the art of perfumery. Many of the natural materials (e.g., galbanum oil) which provide such fragrances and contributes such desired nuanances are high is cost, vary in quality from one batch to another and/or are generally subject to the usual variations of natural products. Indeed, at times, galbanum oil itself has been impossible to obtain at any price.

In the course of the last five years, particularly, an increasing amount of attention has been devoted to the preparation and utilization of artificial perfuming an odor modifying agents possessing the aroma attributes of galbanum oil.

Thus, U.S. Pat. No. 4,449,007 issued on May 15, 1984 discloses a synthesis of the compound having the structure:

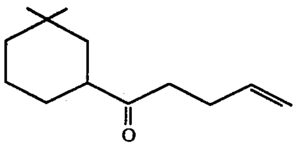

which has useful galbanum-like fragrance nuances.

U.S. Pat. No. 4,117,015 issued on Sept. 26, 1978 discloses the use in perfumery of the compound having the structure:

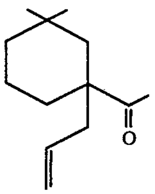

in conjuction or in combination with minor quantities of the compound having the structure:

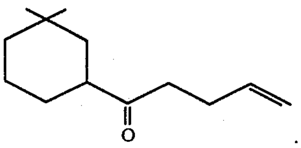

Moderately "weak" galbanum type materials are being marketed including the compound having the structure:

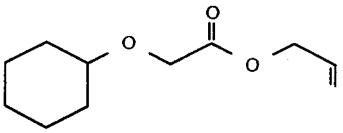

(marketed as "CYCLOGALBANATE" by Dragoco S.A. of West Germany) and allyl amyl glycolate having the structure:

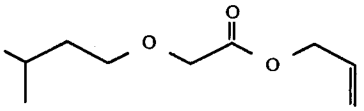

(marketed by International Flavors & Fragrances Inc.). Thus far to date, the only synthetic materials having strong galbanum fragrance nuanaces are the compound having the structure:

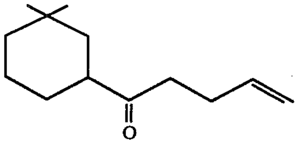

and the compound having the structure:

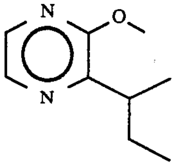

also known as "pepper pyrazine".

Thus, the "closest" compound of the "prior art" is the compound having the structure:

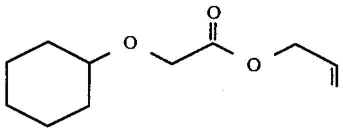

but the compound having the structure:

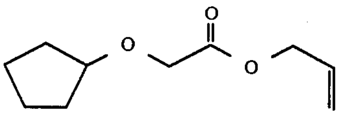

has unexpected, unobvious and advantageous aroma properties (e.g., strength and substantivity) with respect to the compound having the structure:

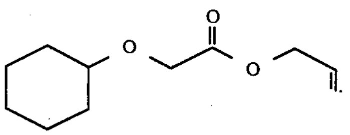

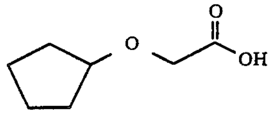

(conditions: SE-30 column programmed at 180° C. isothermal).

Figure 2:
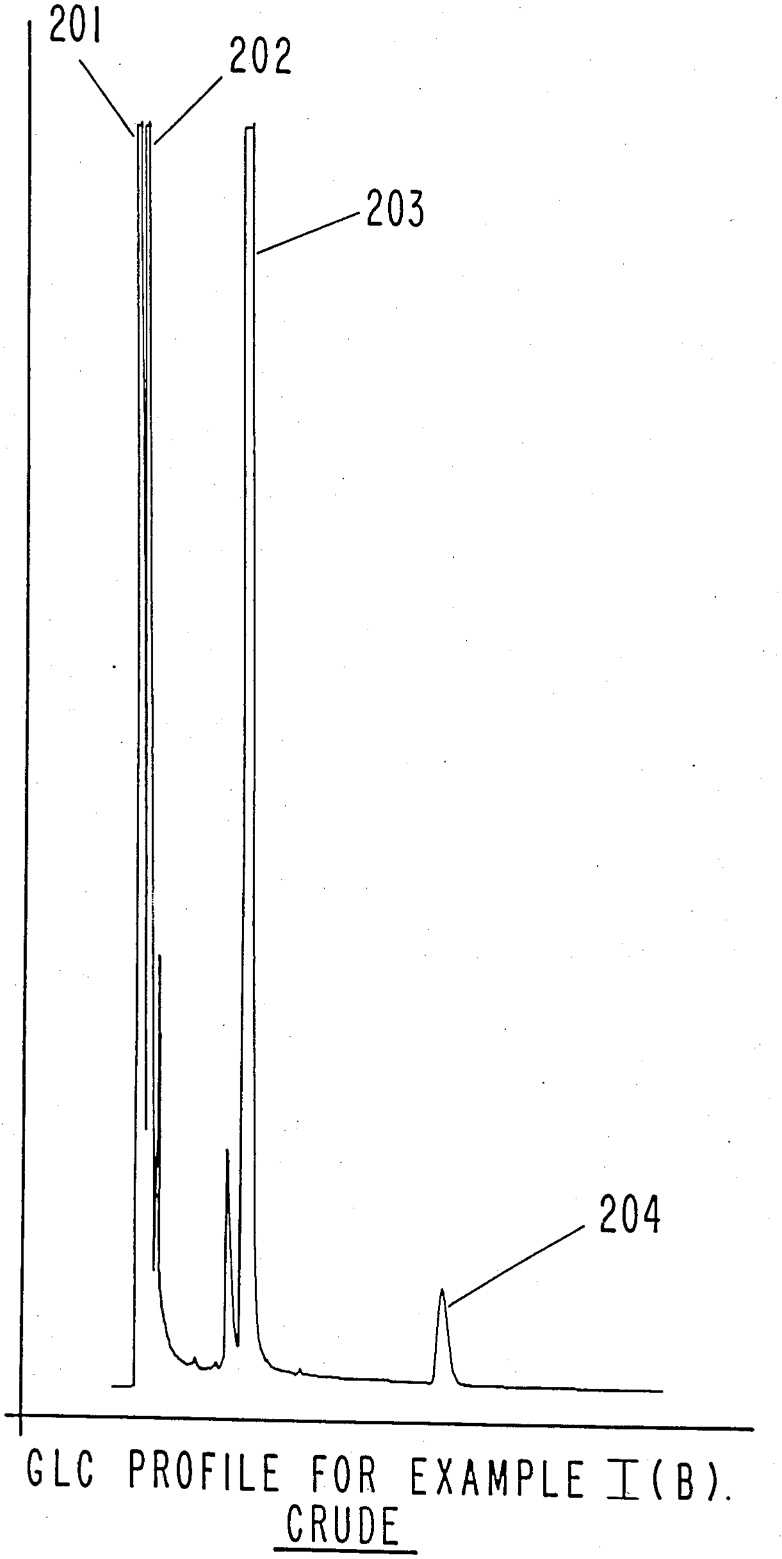

FIG. 2 is the GLC profile for the crude reaction product of Example I (B) containing the compound having the structure:

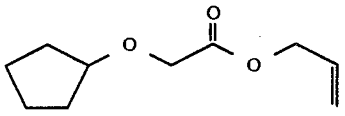

as well as the compound having the structure:

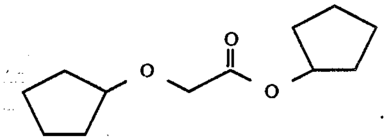

Figure 3:
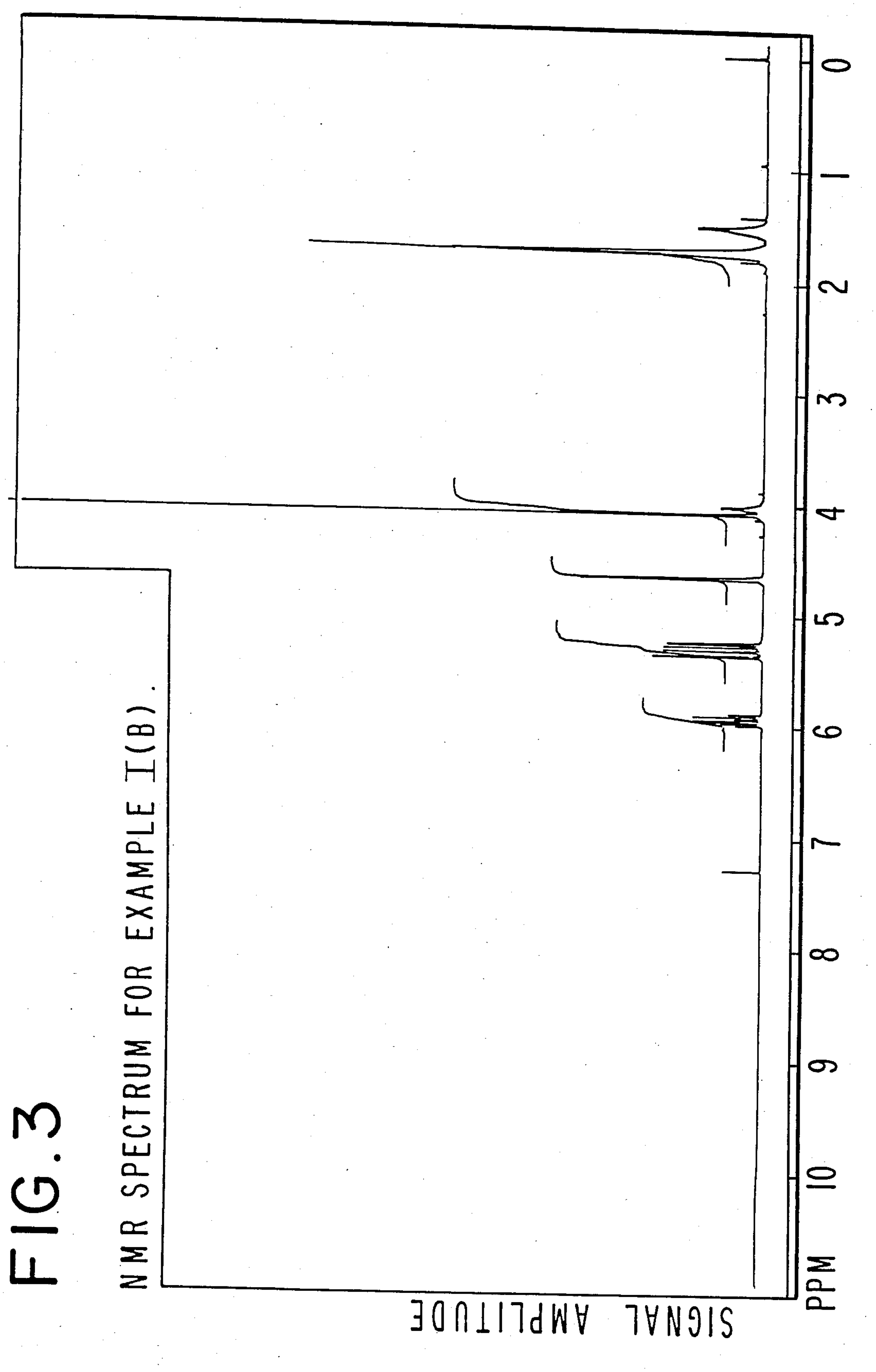

FIG. 3 is the NMR spectrum for the compound having the structure:

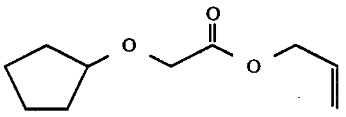

prepared according to Example I (B).

FIG. 4 represents a cut-away side elevation view of apparatus used in forming perfumed polymers which contain imbedded therein the allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention.

FIG. 5 is a front view of the apparatus of FIG. 4 looking in the direction of the arrows.

DETAILED DESCRIPTION OF THE DRAWINGS

Figure 1:
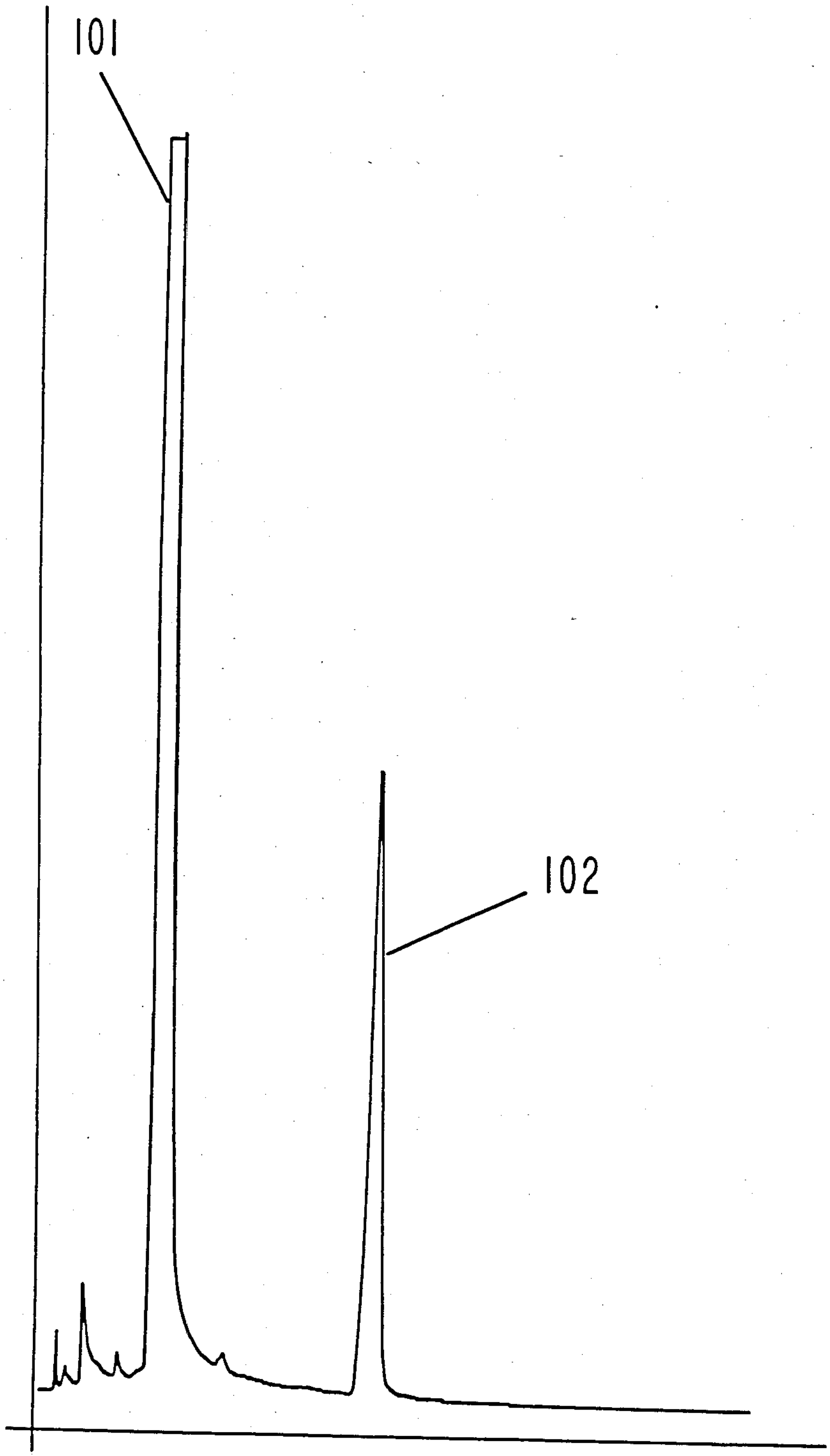
FIG. 1 is the GLC profile for the crude reaction product of Example I (A) containing the compound having the structure.

FIG. 1 is the GLC profile for the crude reaction product of Example I (A) (Conditions: SE-30 columnm programmed at 180° C. isothermal). The peak indicated by reference numeral 101 is the peak for the toluene solvent. The peak indicated by reference numeral 102 is the peak for the compound having the structure:

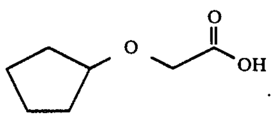

FIG. 2 is the GLC profile for the crude reaction product of Example I (B) (Conditions: SE-30 column programmed at 180° C. isothermal). The peak indicated by reference numeral 201 is the peak for allyl alcohol, a reactant. The peak indicated by reference numeral 202 is the peak for the toluene reaction solvent. The peak indicated by reference numeral 203 is the peak for the reaction product having the structure:

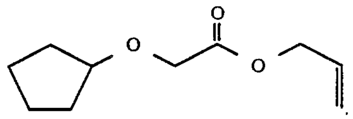

The peak indicated by reference numeral 204 is the peak for the biproduct having the structure:

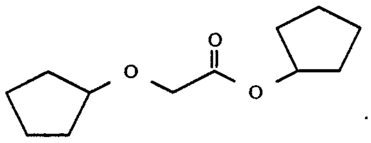

Referreing to FIGS. 4 and 5 there is provided a process for forming scented polymer elements (wherein the polymer may be a thermolplastic polymer such as low density polyethylene or polypropylene or copolymers of ethylene and vinyl acetate or mixtues of polymers and copolymers such as copolymers of ethylene and vinyl acetate and, in addition, polyethylene) such as pellets useful in the formation of plastic particles, useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 4 and 5, in particular, the apparatus used in producing such elements comprises a device for forming the polymer containing perfume, e.g., polyethylene or polyethylenepolyvinyl acetate or mixtues of same or polypropylene, which comprises a vat or container 212 into which the polymer taken alone or in admixture with other copolymers and the perfuming substance which is at least one of the allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention and other compatible perfumes, is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heated coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°-270° C.

Thus, the polymer or mixture of polymers added to the container 212 heated from 10-12 hours, whereafter the perfume composition or perfume material which contains one or more of the allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention is quickly added to the melt. Generally, about 10-45 percent by weight of resulting mixture of the perfumery substance is added to the polymer.

After the perfume material is added to the container 212, the mixture is stirred for a few minutes, for example, 5-15 minutes, and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with the allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention or mixture of perfume substance and the allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention, will continuously drop through the orifices of 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance which is all of or which contains the allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention provides the compound, the allyl ester of 2-cyclopentyloxyacetic acid having the structure:

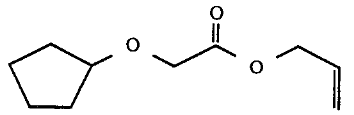

and mixtures of same with 3,3-dimethyl-1-penten-4-oyl cyclohexane having the structure:

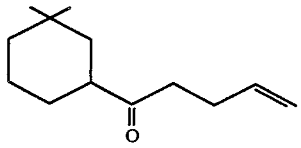

and/or methoxyisobutyl pyrazine having the structure:

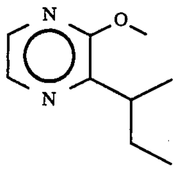

and/or 1-(2-propenyl)-1-acetyl-3-dimethylcyclohexane having the structures:

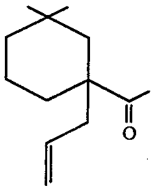

and uses thereof in augmenting or enhancing the aroma of perfume compositions, colognes and perfumed articles (e.g., solid or liquid anionic, cationic, nonionic or zwitterionic detergents, fabric softener compositions, fabric softener articles, perfumed polymers and cosmetic powders).

Also described is a process for preparing the allyl ester of 2-cyclopentyloxyacetic acid having the structure:

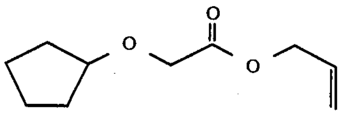

using as starting materials cyclopentanol and an alkali metal salt of a halo acetic acid.

Thus, cyclopentanol is reacted with an alkali metal hydride having the structure:

$M^{\oplus}H^{\ominus}$ according to the reaction:

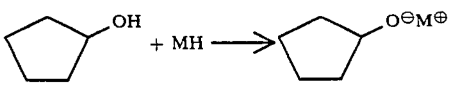

whereby the alkali metal salt of cyclopentanol is produced wherein M is alkali metal. The resulting alkali metal salt of cyclopentanol is then reacted with an alkali metal salt of a halo acetic acid to yield an alkali metal salt of cyclopentyloxyacetic acid according to the reaction:

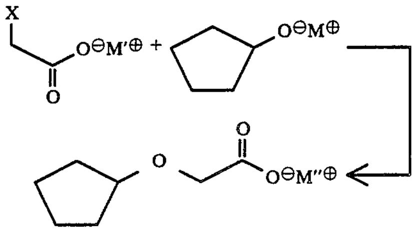

wherein X represents chloro, bromo or iodo; wherein M represents alkali metal; wherein M' represents an alkali metal which is the same or different from M; and wherein M" represents one or a mixture of the alkali metals, M' and M.

The resulting alkali metal salt of the cyclopentyloxyacetic acid having the structure:

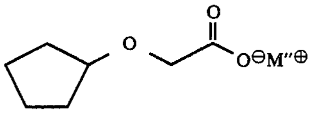

is then acidified and reacted with allyl alcohol under esterification conditions to yield the allyl ester of cyclopentyloxyacetic acid having the structure:

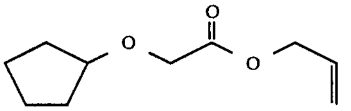

according to the reaction:

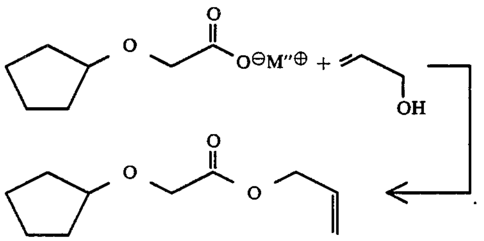

The alkali metal that may be used and is represented by M, M' or M" may be sodium, potassium or lithium. The moiety X is a halogen which may be either or chloro, bromo or iodo.

The reactant MH is most preferably sodium hydride whereby the reaction:

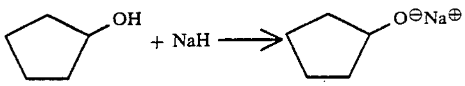

is the preferable reaction in order to form the salt:

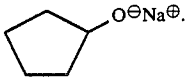

The most preferable alkali metal salt of a halo acetic acid is the compound having the structure:

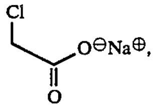

sodium chloro acetate which would enable the most preferred reaction to take place:

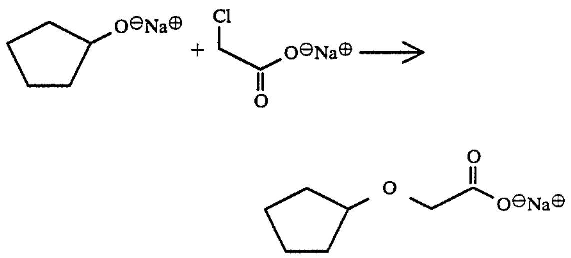

The resulting preferred salt having the structure:

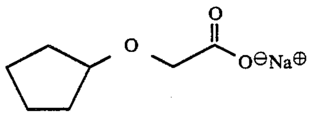

is then acidified using an acid such as hydrochloric acid to form the free acid, cyclopentyloxyacetic acid according to the reaction:

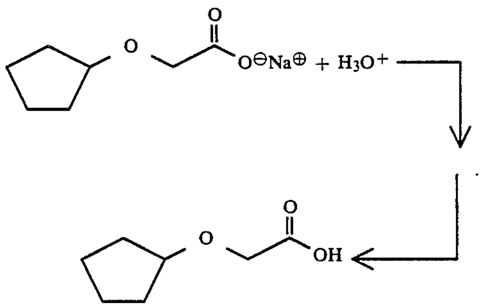

The acid is then esterified with allylic alcohol in the presence of an esterification reagent such as concentrated sulfuric acid according to the reaction:

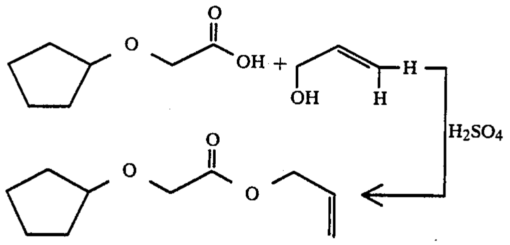

whereby the compound having the structure:

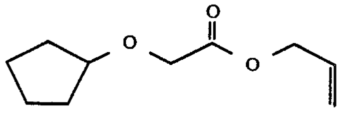

is formed.

The resulting product is preferably fractionally distilled in order to yield an organoleptically efficacious ester, the allyl ester of 2-cyclopentyloxyacetic acid having the structure:

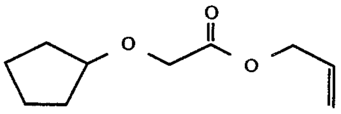

The reaction of the cyclopentyl alcohol with the alkali metal hydride, to wit:

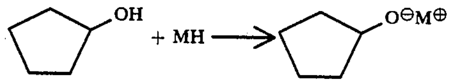

wherein M is alkali metal takes place at a temperature in the range of from about 50° up to about 80° C. in the presence of a solvent which is inert to the reaction product as well as the reactants such as toluene. The reaction time takes place over a period of between one and about five hours at reflux conditions whereby the reaction product, hydrogen is removed from the reaction mass.

The resulting product having the structure:

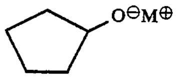

is reacted with an alkali metal salt of a halo acetic acid according to the reaction:

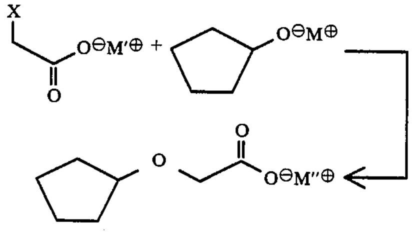

as set forth supra wherein M' is the same or different alkali metal as M and M'' is the same as M' or M and wherein X is chloro, bromo or iodo. The reaction takes place to reflux conditions over a period of between about two and about five hours. The resulting product having the structure:

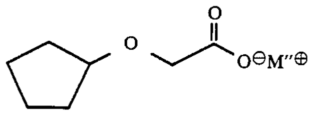

is then acidified prior to being esterified whereby the compound having the structure:

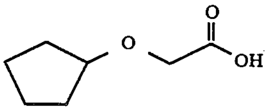

is formed (prior to esterification) according to a reaction such as:

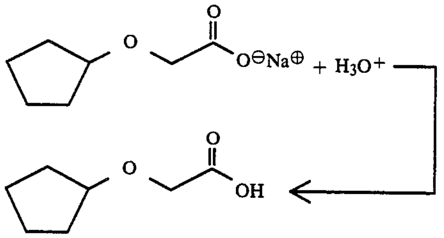

and the resulting acid is then esterified under standard esterification conditions with allyl alcohol to form the ester according to the reaction:

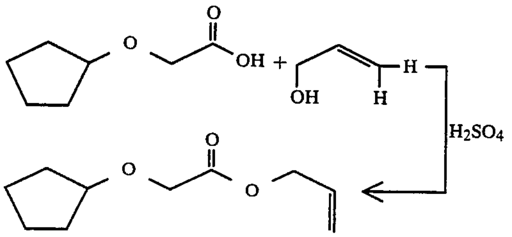

with the overall reaction being shown thusly:

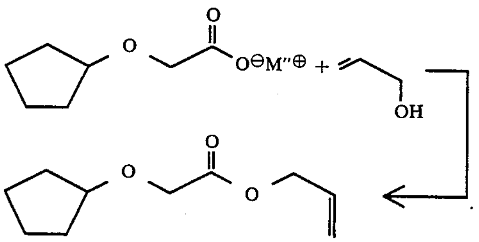

The acidification takes place at ambient conditions using an acid such as hydrochloric acid. The esterification following the acidification takes place at reflux conditions in the presence of an esterification reagent such as concentrated sulfuric acid or para toluene sulphonic acid with allyl alcohol. The mole ratio of allyl alcohol:acid having the structure:

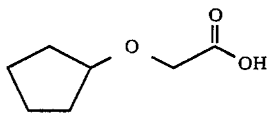

is preferably about 1:1. At the end of the reaction, the resulting product is "worked up" and neutralized with dilute base such as 5% aqueous sodium hydroxide. The resulting product is then distilled as by fractional distillation yielding a product boiling at between 82° and 85° C. (vapor temperature) and 95°-98° C. (liquid temperature) at a pressure of 4.1-4.3 mm/Hg. (as indicated in Example I, infra).

The resulting ester has an interesting rose, green apple and galbanum aroma with intense green, pineapple and galbanum undertones.

It may be used for its perfumery properties alone or in combination with other compounds, e.g., compounds having the structures:

(i) the compound having the structure:

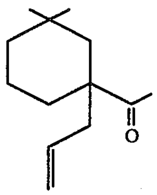

;

and/or (ii) the compound having the structure:

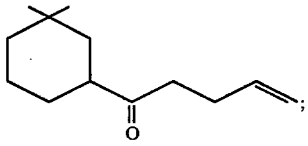

;

and/or (iii) the compound having the structure:

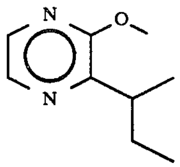

The compound having the structure:

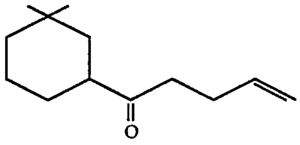

may be prepared according to the process of U.S. Pat. No. 4,449,007 issued on May 15, 1984 the specification for which is incorporated by reference herein.

The compound having the structure:

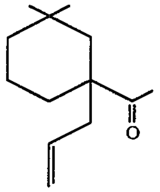

may be prepared according to the disclosure of U.S. Pat. No. 4,117,015 issued on Sept. 26, 1978 the specification for which is incorporated by reference herein.

The allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane prepared in accordance with the process of my invention and one or more auxiliary perfume ingredients including, for example, alcohols, aldehydes, terpenic hydrocarbons, ketones (other than the compounds having the structures:

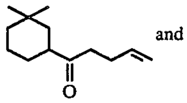

and

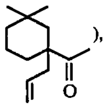

), esters (other than the compound having the structure:

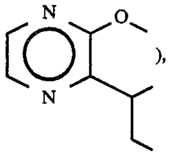

), nitriles, esters other than the ester of my invention, lactones, natural essential oils, synthetic essential oils, mercaptans and alkyl mercapto derivatives may be admixed so that the combined odors of the individual components produce a pleasant and desired fragrance, particularly and preferably in the galbanum type fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual compositions which contribute to their particular olfactory, characteristics, however, the over-all sensory effect of the perfume composition will be at least the sum total of the effects of each of the ingredients. Thus, the allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention can be used to alter, modify or enhance the aroma characteristics of a perfume composition, for example, by utilizing or moderating the olfactory reaction contributed by another ingredient in the composition.

The amount of the allyl ester of 2-cyclopenthyloxyacetic acid, mixtures of same with 3,3-dimethyl-1-penten- 4-oyl cyclohexane and/or methoxyisobutyl pyrazine and/or 3,3-dimethyl-1-(2-propenyl)-1-acetylcyclohexane of my invention which will be effective in perfume compositions as well as in perfumed articles (e.g., solid or liquid detergents, soaps, fabric softener compositions, drier-added fabric softener articles, optical brightener compositions, perfumed polymers textile sizing agents and colognes) depends on many factors, including the other ingredients, their amounts and the effects which are desired. It has been found that perfume compositions containing as little as 0.01% of the allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention and less than 50% of the allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane or even less (e.g., 0.005%) can be used to impart a rose, green apple and galbanum aromas with intense green, pineapple and galbanum undertones to soaps, cosmetics, anionic, nonionic, cationic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

The allyl ester of 2-cyclopentyloxyacetic acid and mixtures of same with 3,3-dimethyl-1-penten-4-oyl cyclohexane and/or methoxysobutyl pyrazine and/or 3,3-dimethyl-1-(2-propenyl)-1-acetylcyclohexane of my invention is useful (taken alone or together with other ingredients in perfume compositions) as (an) olfactory component(s) in detergents and soaps, space odorants and deodorants, perfumes, colognes, toilet water, bath preparations, such as creams, deodrants, hand lotions and sun screens; powders, such as talcs, dusting powders, face powders, and perfumed polymers and articles of manufacture produced from said perfumed polymers. When used as (an) olfactory component of a perfumed article as little as 0.2% of the allyl ester of 2-cyclopentyloxyacetic acid or mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention will suffice to impart an intense rose, green apple and galbanum aromas with intense green, pineapple and galbanum undertones to galbanum formulations. Generally, no more than 6% of the allyl ester of 2-cyclopentyloxyactic acid or mixtures of same with 3,3-di-methyl-1-penten-4-oyl cyclohexane and/or methoxyisobutyl pyrazine and/or 3,3-dimethyl-1-(2-propenyl)-1-acetylcyclohexane of my invention based on the ultimate end product is required in the perfumed article composition. Accordingly, the range of the allyl ester of 2-cyclopentyloxyacetic acid or mixtures of same with 3,3-dimethyl-1-penten-4-oyl cyclohexane and/or methoxyisobutyl pyrazine and/or 3,3-dimethyl-1-(2-pro-penyl)-1-acetylcyclohexane in the perfumed article is from about 0.2% by weight of the allyl ester of 2-cyclopentyl-oxyacetic acid or mixtures of same with 3,3-dimethyl-1-penten-4-oyl cyclohexane and/or methoxyisobutyl pyrazine and/or 3,3-dimethyl-1-(2-propenyl)-1-acetylcyclohexane based on the perfumed article up to about 6% by weight based on the perfumed article. In addition, the perfume composition or fragrance composition of my invention can contain a vehicle or carrier for the allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention. The vehicle can be a liquid, such as non-toxic alcohol, e.g., ethyl alcohol, a non-toxic glycol, e.g., porpylene glycol or the like. The carrier can also be an absorbent solid, such as a gum (e.g., gum arabic, guar gum or xanthan gum) or components for encapsulating the composition (such as gletain) as by coacervation; or components for forming a polymer wall around a liquid perfumed center such as a ureaformaldehyde prepolymer.

My invention also relates to the utilization of controlled release technology for the controlled release of perfumes into gaseous enviornments from polymers such as mixtures of epsilon polycaprolactone polymers and polyethylene which poly epsilon caprolactone polymers are defined according to at least one of the structures:

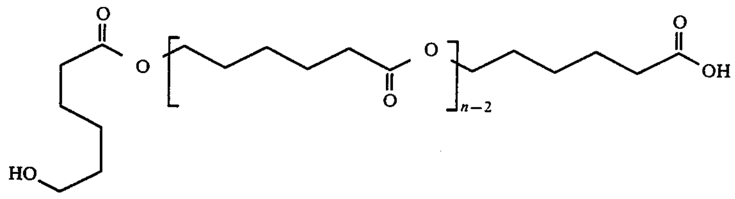

and/or

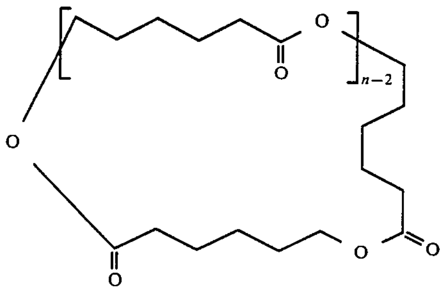

wherein "n" is from about 50 up to about 1,200 with the proviso that the average "n" in the system varies from about 150 up to about 700 according to the mathematical statement:

$$[700 \geq \bar{n} \geq 150]$$

with the term $\bar{n}$ being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$dM_1/dt = k_1 e^{-k_2 t}$$

wherein $k_1$ and $k_2$ are constants. According to Kydonieus, "Controlled Release Technologies:Methods, Theory, and Applications" (cited, supra), the amount of perfume composition released is proportional to time as long as the concentration of perfume material present, e.g., the allyl ester of 2-cyclopentyloxyacetic acid or mixtures of same with 3,3-dimethyl-1-penten-4-oyl cyclohexane and/or methoxyisobutyl pyrazine and/or 3,3-dimethyl-1-(2-Propenyl)-1-acetylcyclohexane of my invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release being constant (zero order) as long as the surface area does not change during the erosion process. This is the case with the polymers containing the allyl ester of 2-cyclopentyloxyacetic acid or mixtures of same with 3,3-dimethyl-1-penten-4-oyl cyclohexane and/or methoxyisobutyl pyrazine and/or 3,3-dimethyl-1-(2-Propenyl)-1-acetylcyclohexane of my invention.

The polyepsilon caprolactone polymers useful in practicing my invention are more specifically described in the brochure of the Union Carbide Corporation, 270 Park Avenue, New York, N.Y. 10017, entitled "NEW POLYCAPROLACTONE THERMOPLASTIC POLYMERS PL-300 ANC PCL-700". These polyepsilon caprolactone polymers are composed of a repeating sequence of non-polar methylene groups and relatively polar ester groups. The average number of repeating monomeric units varies between 150 and 700 depending on the particular "PLC" number. Thus, regarding PCL-300 the average number of repeating monomeric units is about 300. Regarding PCL-700, the average number of repeating monomric units is 700.

The polyepsilon caprolactone homopolymers which are ultimately taken in admixture with such materials as polyethylene useful in the practice of my invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with my invention against discoloration are dihydroxybenzenes such hydroquinone or compounds having the formula:

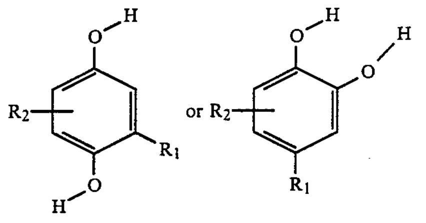

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfere with the functional fluids dissolved and/or adsorbed into the polymeric matrix.

The method for incorporating the allyl ester of 2-cyclopentyloxyacetic acid or mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention or perfume compositions containing same into the polymers may be according to the technique of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thusm, for example, a first amount of liquid polyethylenepolyepsilon caprolactone polymer mixture (50:50) is mixed with the allyl ester of 2-cyclopentyloxyacetic acid or mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of my invention the imparting of scent is effected in two stages. In a first stage, a 50:50 (weight:weight) polyepsilon caprolactone, e.g., PCL-700: polyethylene in molten form is admixed with a high percentage of the allyl ester of 2-cyclopentyloxyacetic acid or mixtures of same with 3,3-dimethyl-1-penten-4-oyl cyclohexane and/or methoxyisobutyl pyrazine and/or 3,3-dimethyl-1-(2-propenyl)-1-acetylcyclohexane of my inventon and mixture is solidified in the form of pellets or beads. These pellets or beads thus contain a high percentage of allyl ester of 2-cyclopentyloxyacetic acid or mixtures of same with 3,3-dimethyl-1-penten-4-oyl cyclohexane and/or methoxyisobutyl pyrazine and/or 3,3-dimethyl-1-(2-propenyl)-1-acetylcyclohexane (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention the allyl ester of 2-cyclopentyloxyacetic acid or mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention is added to the polymer in a large closed container or drum which is maintained under controlled temperature conditions while the polymer in a melted condition is mixed with the allyl ester of 2-cyclopentyloxyacetic acid, mixtures of same with 3,3-dimethyl-1-penten-4-oyl cyclohexane and/or methoxyisobutyl pyrazine and/or 3,3-dimethyl-1-(2-propenyl)-1-acetylcyclohexane of my invention under agitation.

The following Example I serves to illustrate a process for preparing the ester of my invention having the structure:

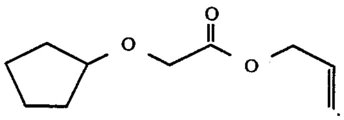

The examples following Example I are illustrative of the organoleptic utilities of the ester of my invention. All parts and percentages given herein are by weight unless otherwise specified.

EXAMPLES I(A) AND I(B)

PREPARATION OF ALLYL ESTER OF 2-CYCLOPENTYLOXYACETIC ACID

Reactions:

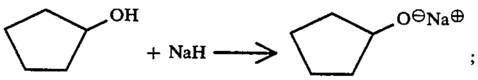

(i) ;

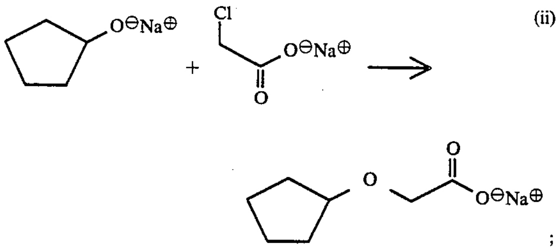

(ii) ;

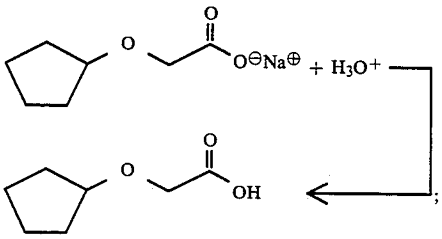

(iii) ;

and

-continued

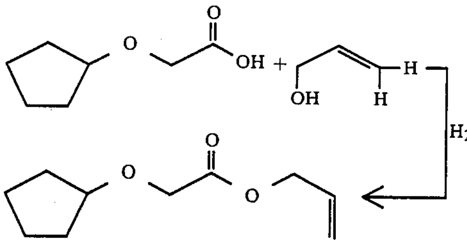

(iv)

EXAMPLE I(A)

Into a 3 liter reaction flask equipped with stirrer, thermometer, reflux condenser and heating mantle are placed 1 liter of toluene and 400 grams of sodium hydride.

The reaction mass is heated to 60° C. and over a period of 1.5 hours, 1,000 grams of cyclopentanol is added to the reaction mass. At the end of the 1.5 hour period, the reaction mass is refluxed until hydrogen generation ceases.

Over a period of one hour, 1,392 grams of the sodium salt of chloroacetic acid is added to the reaction mass. The reaction mass is then quenched by pouring same into 8 liters of water and sufficient concentrated hydrochloric acid is added to bring the pH to less than 2 (856 ml).

The reaction mass now exists in two phases; an organic phase and an aqueous phase.

The organic phase is separated from the aqueous phase and the organic phase is placed in a 5 liter reaction vessel.

EXAMPLE I(B)

The organic phase is then placed in a 5 liter reaction vessel and admixed with 1,000 grams of allyl alcohol and 25 grams of concentrated sulfuric acid. The reaction mass is then heated to reflux and refluxed for a period of three hours using a Bidwell trap to trap out the water of reaction. The reaction mass is then cooled and 2 liters of water are added. The organic phase is separated from the aqueous phase and the organic phase is washed with 1 liter of a 5% aqueous sodium hydroxide solution.

The reaction mass is then distilled in a 12"×1.5" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 23/ | 23/ | 200 | 100% | 785.7 |
| 2 | 40 | 110 | 25 | 100% | 213.4 |
| 3 | 85 | 100 | 5 | 9:1 | 33.9 |
| 4 | 85 | 97 | 4.3 | 4:1 | 49.1 |
| 5 | 85 | 97 | 4.3 | 4:1 | 45.2 |
| 6 | 86 | 97 | 4.3 | 4:1 | 45.0 |
| 7 | 83 | 95 | 4.1 | 4:1 | 45.3 |
| 8 | 82 | 95 | 4.1 | 4:1 | 50.5 |
| 9 | 82 | 97 | 4.1 | 4:1 | 53.6 |
| 10 | 82 | 97 | 4.1 | 4:1 | 51.0 |
| 11 | 82 | 98 | 4.1 | 4:1 | 55.0 |
| 12 | 82 | 98 | 4.1 | 4:1 | 31.3 |

Fractions 6-11 are bulked and the resulting product has a rose, green apple and galbanum aroma with intense green, pineapple and galbanum undertones.

FIG. 1 is the GLC profile for the reaction product resulting from the reaction of sodium chloroacetate and the sodium salt of cyclopentanol. The peak indicated by reference numeral 101 is the peak for toluene. The peak indicated by reference numeral 102 is the peak for the compound having the structure:

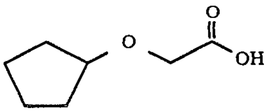

(Example I(A))

FIG. 2 is the GLC profile for the crude reaction product prior to distillation. The peak indicated by reference numeral 201 is the peak for the allyl alcohol reactant. The peak indicated by reference numeral 202 is the peak for the toluene solvent. The peak indicated by reference numeral 203 is the peak for the reaction product having the structure:

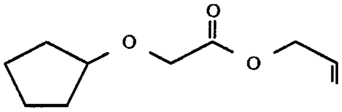

(Example I(B))

The peak indicated by reference numeral 204 is the peak for the biproduct having the structure:

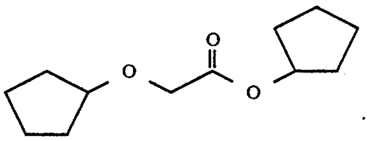

FIG. 3 is the NMR spectrum for the compound having the structure:

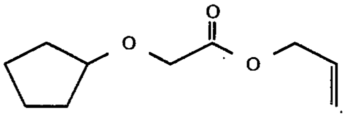

EXAMPLE II

Galbanum Formulation

The following galbanum formulation is prepared:

| Ingredients | Parts by Weight |
|---|---|
| Compound having the structure: 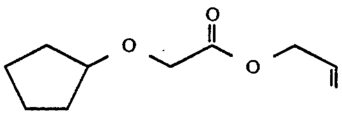 (bulked fractions 6-11 produced according to Example I(B)). | 24.0 |
| Compound having the structure: | 12.0 |

-continued

| Ingredients | Parts by Weight |
|---|---|
| 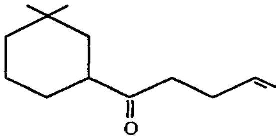 | |
| Compound having the structure: 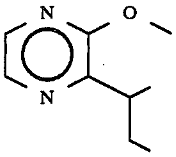 | 14.0 |
| Compound having the structure: 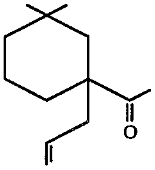 | 06.0 |
| Rose oxide | 03.0 |
| Amyl Cinnamic Aldehyde | 04.0 |
| Geraniol | 03.0 |
| Citronellol | 05.5 |
| Oakmoss Resin | 00.5 |
| Ylang Oil | 18.0 |
| Phenylethyl Acetate | 14.2 |

The resulting product is an excellent galbanum formulation containing rose and green apple topnotes and green and pineapple undertones. Thus, the resulting formulation can be described as "natural galbanum with intense rose and green apple topnotes and intense green and pineapple undertones".

EXAMPLE III

Preparation of Cosmetic Powder Compositions

Cosmetic powder compositions are prepared by mixing in a ball mill 100 grams of talcum powder with 0.25 grams of each of the substnaces set forth in Table I below. Each of the cosmetic powder compositions has an excellent aroma as described in Table I below:

TABLE I

| Substance | Aroma Description |
|---|---|
| Compound having the structure: 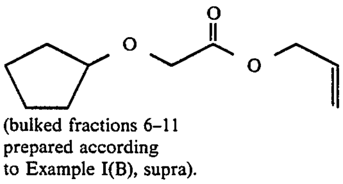 (bulked fractions 6-11 prepared according to Example I(B), supra). | A rose, green apple and galbanum aroma with intense green, pineapple and galbanum undertones. |
| Perfume formulation of Example II. | Natural galbanum with intense rose and green apple topnotes and intense green and |

TABLE I-continued

| Substance | Aroma Description |
|---|---|
| | pineapple undertones |

EXAMPLE IV

Perfumed Liquid Detergents

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table I of Example III, supra are prepared containing 0.10%, 0.15%, 0.20%, 0.25%, 0.30% and 0.35% of the substance as set forth in Table I of Example III, supra. They are prepared by adding and homogeneously mixing the appropriate quantity of substance set forth in Table I of Example III, supra in the liquid detergent. The detergents all possess excellent aromas as set forth in Table I of Example III, supra, the intensity increasing with greater concentrations of substance as set forth in Table I of Example III, supra.

EXAMPLE V

Preparation of Colognes and Handkerchief Perfumes

Compositions as set forth in Table I of Example III, supra, are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example III, supra, are imparted to the colognes and to the handkerchief perfumes at all levels indicated.

EXAMPLE VI

PREPARATION OF SOAP COMPOSITIONS

One hundred grams of soap chips (per sample) IVORY®, producted by the Procter & Gamble Company of Cincinnati, Ohio), are each mixed with one gram samples of substances as set forth in Table I of Example III, supra, until homogeneous compositions are obtained. In each of these case, the homogeneous compositions are heated under 8 atmospheres pressure at 180° C. for a period of three hours and the resulting liquids are placed into soap molds. The resulting soap cakes, on cooling, manifest aromas as set forth in Table I of Example III, supra.

EXAMPLE VII

PREPARATION OF SOLID DETERGENT COMPOSITIONS

Detergents are prepared using the following ingredients according to Example I of Canadian Patent No. 1,007,948 (incorporated herein by reference):

| Ingredient | Percent By Weight |
|---|---|
| Neodol ® 45-11 (a $C^{14}$-$C^{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table I of Example III, supra. Each of the detergent samples has an excellent aroma as indicated in Table I of Example III, supra.

EXAMPLE VIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolved" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example III, supra.

Fabric softening compositions prepared according to Example I at column 15 of U.S. Pat. No. 3,632,396 having aroma characteristics as setforth in Table I of Example III, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example III, supra, is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table I of Example III, supra.

EXAMPLE IX

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of the polymer is dissolved in the alcohol. The following ingredients are added to the PVP/VA alcoholic solution:

| Ingredients | Weight Percent |
|---|---|
| Dioctyl substrate | 0.05 |
| Benzyl alcohol | 0.10 |
| Dow Corning 473 fluid (prepared by the Dow Corning Corporation) | 0.10 |
| Tween 20 surfactant (prepared by ICI America Corporation | 0.03 |
| One of the perfumery substances as set forth in Table I of Example III, | 0.10 |

-continued

| Ingredients | Weight Percent |
|---|---|
| Supra. | |

The perfume substances as set forth in Table I of Example III, supra, add aroma characteristics as set forth in Table I of Example III, supra, which are rather intense and aesthetically pleasing to the users of the soft-feel, good-hold pump hair sprays.

EXAMPLE X

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat® 755N polymer (manufacture by GAF Corporation of 140 West 51st Street, New York, N.Y. (5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 wt ratio of A:B and cooled to 45° C. and 0.3 wt percent of perfuming substance as set forth in Table I of Example III, supra, is added to the mixture. The resulting mixture is cooled to 40° C. and blending is carried out for an additional one hour in each case. At the end of this blending period, the resulting material has a pleasant fragrance as indicated in Table I of Example III, supra.

EXAMPLE XI

Each of the fragrance materials of Table I of Example III, supra, are added to a 50:50 weight:weight mixture of low density polyethylene:polyepsilon caprolactone PCL-700 forming pellets with scents as set forth in Table I of Example III, supra.

75 Pounds of a 50:50 mixture of PCL-700 polyepsilon caprolactone (manufactured by the Union Carbide Corporation of New York, N.Y. having a melting point of about 180°-190° F.):Low density polyethylene, are heated to about 250° F. in a container of the kind illustrated in FIGS. 4 and 5. 25 Pounds of each of the fragrance materials as set forth in Table I of Example III, supra, is then quickly added to the liquified polymer mixture, the lid 228 is put in place and the agitating means 273 are actuated. The temperature is then raised to about 250° F. and the mixing is continued for 5-15 minutes. The valve "V" is then opened to allow flow of the molten polymer enriched with perfume ingredient to exit through the orifices 234. The liquid falling through the orifices 234 solidifies almost instantaneously upon impact with the moving cooled conveyor 238. Polymer beads or pellets 244 having pronounced scents as described in Table I of Example III, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table I of Example III, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table I of Example III, supra.

What is claimed is:

1. The compound having the structure:

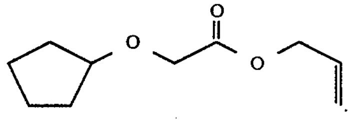

2. A process for augmenting or enhancing the aroma of a perfume composition, a cologne or a perfumed article comprising the step of adding to said perfume composition, cologne or perfumed article, an aroma augmenting or enhancing quantity of the compound of claim 1.

3. The process of claim 2 wherein the compound having the structure:

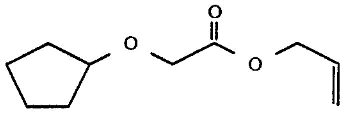

is added to a perfumed polymer.

4. The process of claim 2 wherein the compound having the structure:

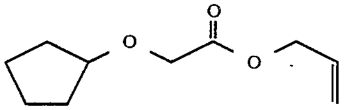

is added to a fabric softener composition or drier-added fabric softener article.

5. The process of claim 2 wherein the compound having the structure:

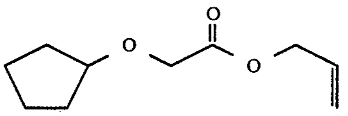

is added to a perfumed article and the perfumed article is a solid or liquid anionic, cationic, nonionic or zwitterionic detergent.

* * * * *